United States Patent [19]
Baron

[11] Patent Number: 4,506,663
[45] Date of Patent: Mar. 26, 1985

[54] FINGER SUCKING PREVENTIVE DEVICE

[76] Inventor: Walter Baron, 28 Bayville Park Blvd., Bayville, Long Island, N.Y. 11709

[21] Appl. No.: 432,094

[22] Filed: Sep. 30, 1982

[51] Int. Cl.³ .............................................. A61F 13/00
[52] U.S. Cl. .................................................. 128/133
[58] Field of Search ...................... 128/133, 252, 89 R

[56] References Cited

U.S. PATENT DOCUMENTS

| | | | |
|---|---|---|---|
| 2,633,126 | 3/1953 | Newmark | 128/133 |
| 3,334,025 | 8/1967 | Baron | 128/133 |
| 3,850,167 | 11/1974 | Steeley | 128/89 R X |
| 4,396,014 | 8/1983 | Pace et al. | 128/133 |

Primary Examiner—Stephen C. Pellegrino
Attorney, Agent, or Firm—Browdy and Neimark

[57] ABSTRACT

A finger sucking preventive device adapted to be applied peripherally of a finger has two elongate, flexible strips with an elongate, flexible corrugated element sandwiched therebetween. The corrugations of the corrugated element are disposed transversely to the length of the strips to form transverse air passages therebetween. Preferably the corrugated element has curved portions on one side connected by flat portions on the other side, the flat portions being arranged to bear against the finger. For securing the device in the form of a loop around the finger, the external surface of the inner strip may be provided with an adhesive coating, and adhesively coated tabs preferably extend from both ends of the device.

3 Claims, 6 Drawing Figures

U.S. Patent     Mar. 26, 1985     4,506,663
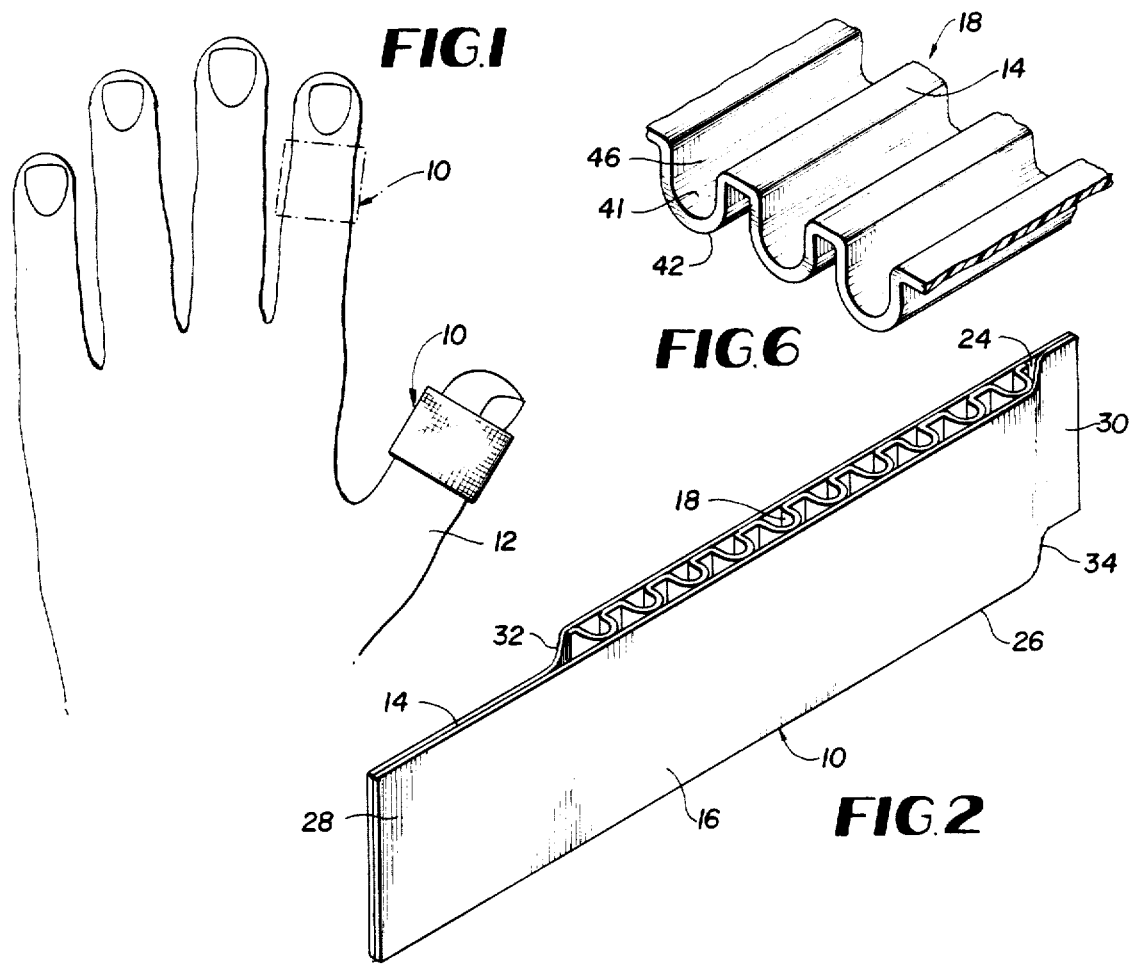
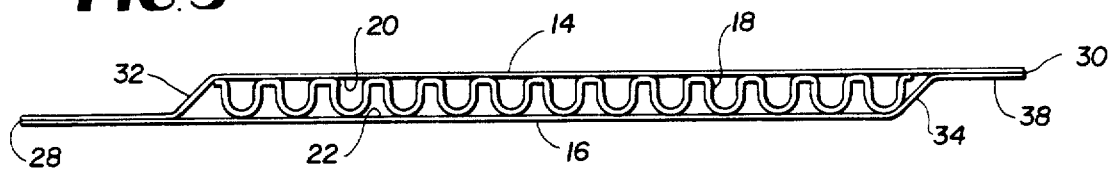
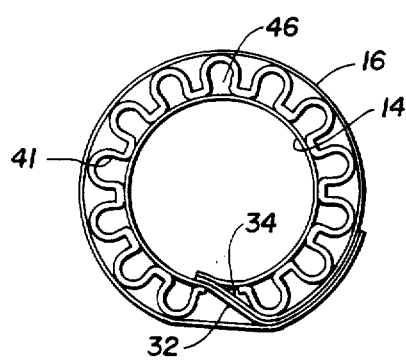
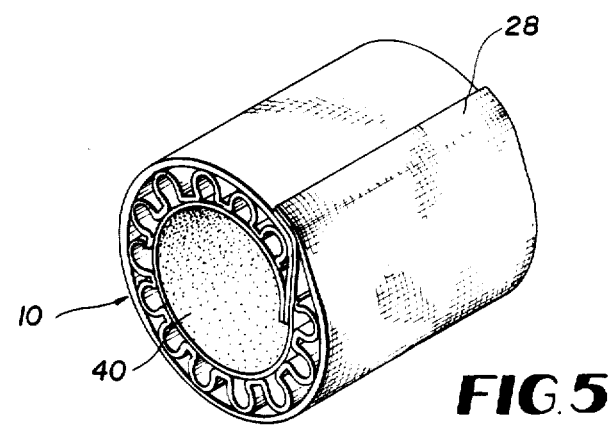

FINGER SUCKING PREVENTIVE DEVICE

FIELD OF THE INVENTION

This invention relates to finger sucking deterrents for children and more particularly to an improved finger sucking preventive device.

BACKGROUND OF THE INVENTION

The objections to finger sucking, especially by infants, are numerous. To curtail this prevalent habit in children can preclude malformation of facial features by avoiding deformation or irregularities of the teeth, so preserving the aesthetic value of normal tooth development, and also eliminating the inferiority behaviour pattern often associated with finger sucking.

In my earlier U.S. Pat. No. 3,334,625, which is hereby incorporated by reference, is disclosed a finger sucking preventive device having a plurality of parallel slats secured between two flexible, superimposed strips, the device in use being applied to the finger by being wrapped therearound in the form of a loop. The spaces between the transverse slats provide air passages whereby any vacuum otherwise created during the practice of finger sucking will be destroyed to the end of removing the pleasure normally derived by such practice.

SUMMARY OF THE INVENTION

It is an object of the present invention to provide an improved finger sucking preventive device which ensures better air passage in use when applied to the finger.

Another object of the present invention is to provide an improved finger sucking preventive device in which the air passages can more readily be kept clean.

A feature by which these objects are achieved is the replacement of the slats by a flexible, corrugated filler member. This has the advantage that the corrugations form air passages that retain their integrity and do not tend to flatten when the device is applied around the finger so ensuring better air passage and more readily cleanable air channels.

Accordingly, there is provided by the present invention a finger sucking preventive device adapted to be applied peripherally of the finger and having two elongate, flexible strips with an elongate, flexible corrugated element sandwiched therebetween. The corrugations of the corrugated element are disposed transversely to the length of the strips to form transverse air passages therebetween.

Preferably, the corrugated element has curved portions on one side connected by flat portions on the other side, the flat portions being arranged to bear against the finger.

An adhesively coated tab preferably extends from each end of the device.

Other objects, features and advantages of the present invention will become more fully apparent from the following detailed description of the preferred embodiment, the appended claims and the accompanying drawing.

BRIEF DESCRIPTION OF THE DRAWING

In the accompanying drawing:

FIG. 1 is an illustrative view of a finger sucking preventive device according to the present invention applied to two fingers of a child's hand;

FIG. 2 is a perspective view of the device of FIG. 1 illustrated in the unapplied elongate state;

FIG. 3 is a side elevational view of the device of FIG. 2 in the unapplied elongate state;

FIG. 4 is an end view of the device of FIG. 1 when in the applied operative position but with the finger omitted;

FIG. 5 is a perspective view of the device in the form shown in FIG. 4; and

FIG. 6 is a perspective view, on a larger scale, of a portion of the corrugated filler member of the device.

DETAILED DESCRIPTION OF THE PREFERRED EMBODIMENT

The preferred embodiment of the present invention is illustrated by way of example in the drawing, FIG. 1 showing the finger sucking preventive device designated generally by the reference numeral 10 applied to the thumb 12 of a hand of a child, the left hand. Another device 10 is shown in broken lines applied to the index finger.

FIGS. 2 and 3 show the device 10 in the elongate state before being applied. It comprises two strips 14, 16 of flexible, adhesive material arranged in parallelism whereby opposingly faced sides are disposed in spaced superposed relation. Sandwiched between the two strips or lengths of flexible material 14,16 is a filler member formed by a length of corrugated or channelled element 18 in continuous strip form having the same width as the strips 14, 16 but being a bit shorter in length. The corrugated element 18 is flexible and preferably made of plastic material, preferably low density polyethylene. The element 18 is secured to the strips 14, 16 by adhesive coatings 20, 22 provided on the internal, facing surfaces of the strips 14, 16, respectively. The corrugations of the element 18 are parallel to each other, and extend transversely between the strips 14, 16 from one longitudinal edge 24 of the device 10 to the other longitudinal edge 26 so forming transverse air passages therethrough. As shown, the ends of the strips 14, 16 extend beyond both ends of the corrugated element 18 in the longitudinal direction, and are secured directly together by adhesive to form end tabs 28, 30. These end tabs are offset with respect to each other, and merge into the body of the device 10 with inclined surfaces 32, 34. The inner, upwardly facing surface 36 of the left hand tab 28 and the outer, downwardly facing surface 38 of the right hand end tab 30 have adhesive coatings.

FIGS. 4 and 5 show the device formed into a loop or ring in the form it is when encircling the finger. As can be seen, the tabs 28, 30 overlap the opposing end portions of the strips 14, 16, respectively, with the inclined surfaces 32, 34 being complementary and providing a smooth lapped joint. The adhesive coatings 36, 38 on the tabs 28, 30 secure them to the underlying portion of the strips 16, 14, respectively. An adhesive coating 40 on the exterior surface of the strip 16 covers the entire inner surface of the loop formed device 10 for adherence to the finger when applied therearound.

FIG. 6 shows in greater detail the form of the channels 41 in the corrugated element 18. Each channel 41 has a curved peripheral wall 42 in the form of a circular arc subtending through an angle of at least 180 degrees with flat sections 44 connecting adjacent channels 41.

All the connecting flat sections 44 are disposed on one side of the corrugated element, and it is this side that is applied towards the finger. Thus, the channels 41 in the element 18 are open on the inside towards the finger and are closed on the outside away from the finger, with the inner openings 46 of the channels 41 being sealed over by the inner strip 14. This preferred form of the corrugated element 18 has the advantage that when the device 10 is applied around a finger, the element 18 readily flexes with the flat sections 44 moving closer together and the arcuate walls 42 of the channels becoming more circular in cross-section. Also, the flat sections 44 enable the element to be more strongly adhered to the inner strip by providing a greater area in contact with the adhesive coating 22 and so enabling the element 18 to be more securely held against possible dislodgement. Also, the spaces 46 between the flat surfaces 44 close up when the device 10 is adapted to the finger to form an almost flat continuing surface area that adapts easier to the finger and holds the device 10 more securely thereon.

The flexible strips 14, 16 are preferably composed of conventional adhesive tape material. Strips of such material are sufficiently resilient in the longitudinal direction to allow the inner strip 16 to contract and the outer strip 14 to stretch when the device 10 is applied around the finger.

It will be appreciated that upon applying the device 10 peripherally of a finger as shown in FIG. 1, the development of suction will be prevented when the child draws upon his finger with the latter inserted in his mouth. The air passages 41 establish air vents between the finger and the mouth to thereby preclude the formation of any pleasurable sucking sensation otherwise experienced by the child in the absence of the device 10 about his finger. It has been observed that where the sensation is incapable of effectuation, the finger sucking practice will be discouraged and ultimately the undesirable habit will be eliminated entirely.

When the device 10 is applied, the adhesive coating 40 will secure it securely to the finger, and the smooth, overlapped securement of the end tabs 28, 30 will act to preclude removal of the device 10 through any initial persistent sucking attempts of the child. Removal is also further resisted by the greater holding power of the device provided by the adaptability of the corrugated element 18 with the inner side having flat surfaces and the outer side rounded surfaces.

The somewhat circular cross-sectioned channels 41 do not tend to collapse or flatten against the finger, so providing controlled, efficient openings for air passage and effectively allowing for a greater passage of air. The greater the air flow through the device, the quicker the finger sucking habit can be eliminated.

The channels 41, by resiliently retaining their curved shape, can more easily be kept open and flushed out so reducing the risk of becoming clogged with food or other debris. Also, should the child bite into the device, the resiliency of the channels 41 would cushion the bite, and due to the large number of channels in the device, air would still be able to get through to break the suction of any attempted finger sucking.

By providing an adhesive tab at each end, the device 10 can readily be made to fit all sizes of fingers by adjusting the amount of overlap of the end tabs 28, 30.

Another advantage of the continuous corrugated element 18 is that it simplifies and reduces the cost of assembly. The length of corrugated strip is simply laid on one of the adhesive strips and then the other adhesive strip placed over the corrugated strip.

The above described embodiments, of course, are not to be construed as limiting the breadth of the present invention. Modifications, and other alternative constructions, will be apparent which are within the spirit and scope of the invention as defined in the appended claims.

What is claimed is:

1. A finger sucking preventive device comprising:
two elongate strips of flexible adhesive material arranged in parallelism whereby respective interior adhesive sides thereof are opposingly arranged in spaced superposed relation;
a continuous elongate, flexible corrugated element extending lenthwise between said strips and having its corrugations extending transversely thereof to form air passages therethrough, said corrugated element adhering to said respective interior adhesive sides of said strips;
said corrugations being formed by curved sections on one side of said corrugated element connected by flat sections on the other side;
an adhesively coated tab extending from each end of said device; and
an adhesive coating over the exterior surface of the strip adjacent said flat sections of said corrugated element;
whereby said device can be applied peripherally of a finger and retained therearound in the form of a loop with said flat sections of said corrugated element on the inside of said loop.

2. The device of claim 1, wherein said corrugated element is made of polyethylene.

3. The device of claim 1, wherein said curved sections each comprise at least a semicircle in cross-section.

* * * * *